(12) United States Patent
Clampitt

(10) Patent No.: US 6,403,328 B1
(45) Date of Patent: Jun. 11, 2002

(54) METHOD OF MEASURING ERYTHROCYTE SEDIMENTATION RATE (ESR) OR PLASMA FIBRINOGEN OF A BLOOD SAMPLE

(76) Inventor: Roger Clampitt, Frichedon, Bemel Hempeload, Hertfordshire HP1 3DD (GB)

( * ) Notice: Subject to any disclaimer, the term of this patent is extended or adjusted under 35 U.S.C. 154(b) by 0 days.

(21) Appl. No.: 09/623,340
(22) PCT Filed: Mar. 5, 1999
(86) PCT No.: PCT/GB99/00574
§ 371 (c)(1),
(2), (4) Date: Oct. 16, 2000
(87) PCT Pub. No.: WO99/45363
PCT Pub. Date: Sep. 10, 1999

(30) Foreign Application Priority Data

Mar. 5, 1998 (GB) .............................. 9804560

(51) Int. Cl.⁷ .............................. C12Q 1/56; A01N 1/02; G01N 33/53
(52) U.S. Cl. .............................. 435/13; 435/2; 435/973
(58) Field of Search ............................. 435/13, 2, 973

(56) References Cited

U.S. PATENT DOCUMENTS 4,675,117 A * 6/1987 Neumann et al. ............. 435/13

FOREIGN PATENT DOCUMENTS

WO    9945363 A * 3/1999

\* cited by examiner

Primary Examiner—Louise N. Leary

(57) ABSTRACT

A method of measuring erythrocyte sedimentation rate (ESR), plasma viscosity, or plasma fibrinogen of a blood sample is provided. The method involves treating the blood sample with a suitable anti-coagulant, placing the treated sample in a micro-haemocrit tube and centrifuging the sample at, for example, 500 rpm or greater while continually monitoring the sample using an IR light source and detector to follow appropriate separation band development during centrifugation. Thus, continual monitoring of the sample during the centrifugation process is possible. Preferably, the sample is horizontal throughout the centrifugation process.

10 Claims, 4 Drawing Sheets

METHOD OF MEASURING ERYTHROCYTE SEDIMENTATION RATE (ESR) OR PLASMA FIBRINOGEN OF A BLOOD SAMPLE

This invention relates to a method of measuring erythrocyte sedimentation rate or plasma fibrinogen of a blood sample.

When blood containing an appropriate anticoagulant is allowed to stand, the erythrocytes in the blood aggregate to form regular columns of cells ("rouleaux") which then sediment or sink in the medium. The rate at which this occurs is known as the erythrocyte sedimentation rate (ESR) and is used in veterinary and human medicine primarily as an indicator of or to follow the course of an inflammatory condition (eg rheumatism or tuberculosis). The vast majority of acute or chronic infections, neoplastic and degenerative diseases are associated with changes in the blood which result in an alteration in the ESR.

Conventionally a number of methods of measurement of ESR have been used, including Westergren's method and Wintrobe's method, and these differ as to the anticoagulant used, the volume of blood employed, the dimensions of the tube in which the measurement is carried out, the time allowed for sedimentation to take place and the method of recording the results. However conventional methods rely on the force of gravity for the sedimentation process to take place. The problem associated with these conventional methods is that the test tube must be allowed to stand undisturbed for a significant length of time, for example up to 1 hour or more. The results of the ESR test may be required before this time has elapsed.

An ESR measurement can also be used to obtain information on plasma viscosity. Plasma viscosity can increase for a number of reasons eg dehydration or an increase in globulin concentration. The latter occurs for example in multiple myeloma.

Plasma fibrinogen measurements provide information on inflammatory conditions and may be used in some circumstances as an alternative or a supplement to ESR measurements.

As with known methods of measuring ESR, the known methods of measuring plasma fibrinogen have the associated problem that samples must be left undisturbed for a significant length of time.

A number of attempts to speed up the measurement of ESR have been described in the literature. For example, U.S. Pat. No. 3,824,841 describes the centrifugation of whole blood by spinning vertically orientated columns of blood. This method suggests that the columns should be rotated by 180° a number of times during the centrifugation process. Centrifugation occurs at a speed of 2 to 20 G, preferably 6.25 to 8 G. The centrifuge itself is further described in U.S. Pat. No 3,848,796.

EP-A-0,297,237 describes a centrifuge tube which includes a cylindrical float. After centrifugation of the sample the float settles into the zone occupied by the constituent to be measured and the presence of the float means that there will be axial expansion of that constituent, facilitating more accurate measurement of its volume. The centrifuge tube is described as being suitable for use in, for example, the centrifugation of blood. The use of this system to test for fibrinogen in anticoagulated whole blood is described in U.S. Pat. No. 5,137,832 and the utility of that measurement together with the haemoglobin volume is correlated to diagnosis of systemic inflammation in a mammal in U.S. Pat. No. 5,506,145.

U.S. Pat. No. 5,594,164 describes accelerated rouleaux formation in a specimen of blood by use of centrifugation. Certain publications also describe the possibility of monitoring blood samples and mention may be made of EP-A-0,732,576 in which a blood sample may undergo centrifugation between 2 and 20 G and the optical density of the sample is monitored over time using electromagnetic radiation of wave length 200 to 1000 nm.

WO-A-94/18557 describes an apparatus for centrifuging blood. The centrifuged blood is then monitored through the use of optical means but this occurs only after centrifugation of the sample has been completed.

WO-A-96/39618 describes a method and apparatus for determining ESR through centrifugation of whole blood. A video camera is set up to monitor the blood separating into red blood cells and fluid. The results must be analysed by replaying the video in slow motion.

According to the present invention there is provided a method of measuring erythrocyte sedimentation rate (ESR) or plasma fibrinogen of a blood sample wherein sedimentation of particles in the sample is accelerated by application of a centrifugal force to the sample, characterised in that said measurement is taken during centrifugation of the sample.

The method of the present invention for measuring erythrocyte sedimentation rate (ESR) or plasma fibrinogen in a blood sample involves treating the blood sample with a suitable anti-coagulant, placing the treated sample in a micro-haematocrit tube and centrifuging the sample at, for example, 500 rpm or greater whilst continually monitoring the sample using an IR light source (for example an IR laser) and detector to follow appropriate separation band development during centrifugation. Thus, continual monitoring of the sample during the centrifugation process is possible.

Preferably the centrifugal force is brought about by spinning the sample, for example at speeds of 500 rpm or greater. Conveniently, the sample is placed into a microhaematocrit tube which is sealed and then located in the centrifuge rotor.

Importantly, the microhaematocrit tube containing the blood sample is placed horizontally with its longitudinal axis extending radially from the rotational centre of the centrifuge. For example the tube may be located in slots of the centrifuge rotor sized and shaped so that the microhaematocrit tube sits snugly therein. The light source is positioned a specific distance along the radius of the centrifuge rotor. The exact distance chosen may vary depending upon the radial size of the centrifuge rotor and upon the length of the microhaematocrit tube. Usually, however, the position of the light source is chosen so that separation of the blood sample can be easily monitored.

A sensor is located on the opposite side of the microhaematocrit tube to the light source such that light passing from the light source through the tube would be detected. As the sample is centrifuged, the sensor monitors whether light passes through the microhaematocrit tube or not. Where the portion of the microhaematocrit tube sampled contains whole blood, no light will be detected by the sensor. Where, however, the blood cells have been completely spun down from that portion of the tube, the amount of light detected will be maximal.

Thus, during the process of centrifugation, the red blood cells gradually settle towards the end of the microhaematocrit tube located at the outer edge of the centrifuge rotor. The interface between plasma and red blood cells establishes gradually and moves radially outwardly during the centrifugation process. Where the light source and sensor are static, the plasma/red blood cell interface will move gradually through the light beam and at that stage detection of light by the sensor will commence.

We have found that spinning the sample in a stable horizontal plane permits the establishment of an angled interface. The angle itself will vary depending upon the amount of reticulocytes (immature red blood cells) present in the sample. Reticulocytes are large cells of low density which have previously been noted to cause blurring at the interface during conventional ESR measurements. Determining the approximate concentration of the reticulocytes in a blood sample provides useful information to the clinician. Depending upon the presence or absence of reticulocytes or other low density particles, the angle of the Interface established may be very shallow or almost vertical. Since the method described herein permits the sample to be monitored at very frequent intervals, it is possible to measure (as a function of the percentage light detected) the angle of the slope of the plasma/red blood cell interface and to obtain diagnostic information therefrom.

It is known that occasionally blood precipitates in two or three phases in the traditional ESR procedures. The present methodology allows continual monitoring during the ESR test along the full length of the microhaematocrit tube. In this embodiment the laser or other light source is placed just behind the original blood/air interface of the non-centrifuged sample. As soon as the interface is detected by light passing through the sample, the light source and sensor can be automatically moved radially outwardly a further appropriate distance and this movement of light source and sensor in a radial outward direction can be repeated as necessary to allow monitoring of the separation rate along the full tube length. We have found that moving the light source and sensor in 2 mm steps is adequate. When movement of the light source and sensor occurs, an appropriate compensation to the sensor output is of course made during calculation.

We have observed that the interface takes a period of approximately 1 to 6 seconds to pass through the area monitored by the light source and sensor, depending upon the centrifugation speed chosen and the interface Preferably, when measuring the erythrocyte sedimentation rate, the sample is centrifuged at 500–4,000 rpm for a period of time, usually less than 5 minutes, for example 2 minutes or less. For human blood we have found that a speed of 500–1,200 rpm, usually 500–1,000 rpm, for approximately 3 minutes is usually appropriate.

The exact speed chosen will vary depending upon the species from which the sample was taken. For dog blood, for example, speeds of 3,000–3,500 rpm are suitable whilst for human blood a speed of approximately 500–1,000 rpm has been found to be appropriate. In choosing a centrifugation speed, the aim is to balance the speed of separating the sample with adequate monitoring. Usually a sample time of 30 seconds to 3 minutes is required. Optimal monitoring can be performed at least up to speeds of 4,000 rpm and thus continual monitoring throughout the centrifugation process is possible with the method of the present invention. An important advantage of the present invention is that the sample is monitored at each revolution of the centrifuge rotor and hence a vast quantity of data is obtained.

Preferably where plasma fibrinogen is being measured the sample may be spun twice. The sample may be spun at a rate of approximately 8,000–12,000 rpm, for example 10,500 rpm, to cause speedy separation of the red blood cells from the remainder of the blood. The sample will then normally be incubated at temperatures of between 53–56° C. for 2 to 5 minutes to precipitate the fibrinogen protein. The precipitated sample is then centrifuged again (usually at speeds of 8,000–12,000 rpm, for example 10,500 rpm) and the amount of fibrinogen determined.

Preferably the centrifuge used is chosen so that changes in the blood during centrifugation are measured and calculated automatically by the centrifuge device. This has the advantage that little or no manual intervention is required.

Desirably the changes in the blood sample are automatically monitored through IR emission and detection. The IR radiation is emitted from a suitable source, for example an IR laser, and is directed at the sample. The IR radiation used is desirably of wavelength 650–1000 nm. An IR laser of wavelength 780 has been used successfully. The level of absorbance of the IR radiation by the sample is measured by a sensor. For example, the sensor may detect any IR radiation not absorbed by the sample. For example in whole blood, no IR radiation will be detected (0% detection) since the cells will absorb all of the light. Where the cells of the blood sample have been substantially completely separated so that the IR radiation passes only through residual fluid, absorbance will be minimal and detection of the light source will be considered as 100%. Thus, the level of IR radiation detected may be used to determine the presence of any interface indicating a separation boundary between components of the sample. Usually the interface can be monitored over a period of at least one second, preferably 2 to 10 seconds, usually 1 to 6 seconds. As indicated above, this monitoring process occurs during centrifugation so that no measurement or analysis of the sample is required following centrifugation. Whilst monitoring of the sample at high centrifugation speeds (e.g. 8,000–12,000 rpm) by this methodology is possible, it may be preferred to slow the speed of centrifugation to permit monitoring of the sample at intervals. Where the centrifugal speed exceeds 8,000 rpm, slowing of the centrifuge speed is particularly advisable. Usually, however, continual monitoring of the sample is possible at centrifugal speeds of 500–4,000 rpm.

Preferably the blood sample is of volume less than or equal to 50 $\mu$l, for example is 36 $\mu$l. The blood sample may, for example, come from a finger, thumb or ear lobe prick of a patient. The blood sample will normally be mixed with an anticoagulant prior to being put in the sample tube. Alternatively the sample tube may be provided with an anticoagulant coating internally so that the blood sample may be introduced directly into the tube.

Examples of methods according to the present invention will now be described with reference to the accompanying drawings in which:

FIG. 1a is a plan view of a rotor 4 suitable for employment in the method of the present invention. In the rotor 4 illustrated there are four equidistant spaced slots 2 located in the rotor which is mounted horizontally in the centrifuge. Members 6 engage with the motor of the centrifuge and ensure angular velocity of the rotor. The slots 2 are sized and shaped so that a microhaematocrit tube can be located snugly therein and does not become displaced during centrifugation, even at angular speeds of 12,000 rpm. A small cut-away portion 8 is located at one end of each slot 2 to facilitate removal of the microhaematocrit tubes (not shown). It is important to note that each slot 2 represents a cut-away portion of the rotor which in the absence of any sample being placed therein permits light directed from one side of the rotor to pass through and be detected at the opposite side of the rotor. Usually, the light source will be placed above the rotor and the sensor, underneath the rotor (see for example FIG. 1b) but naturally this arrangement may be reversed if so required.

Figure 1A:
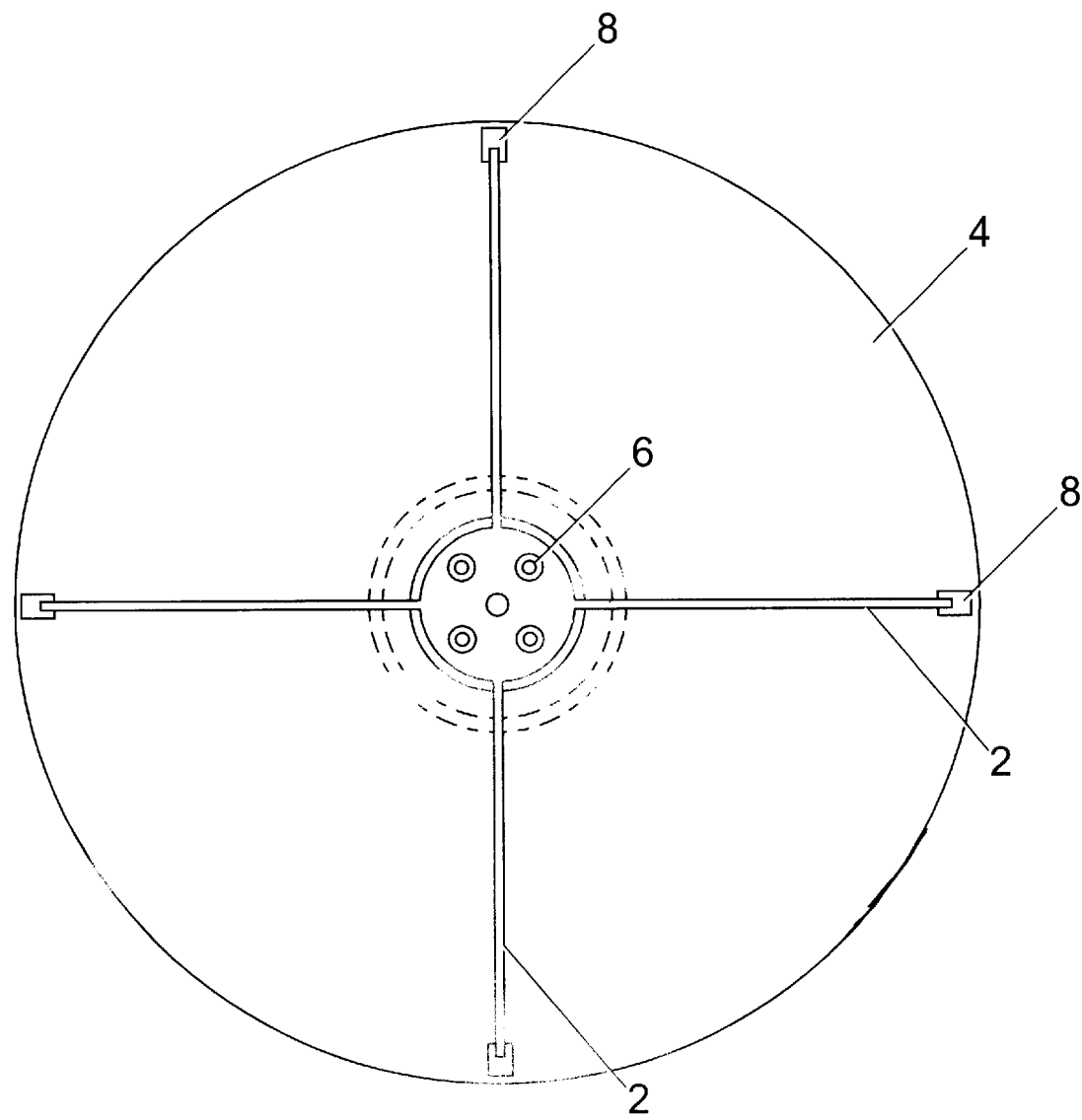
FIG. 1a is a plan view of the centrifuge rotor showing 4 slots therein, each adapted to hold a glass microhaematocrit tube.
Figure 1B:
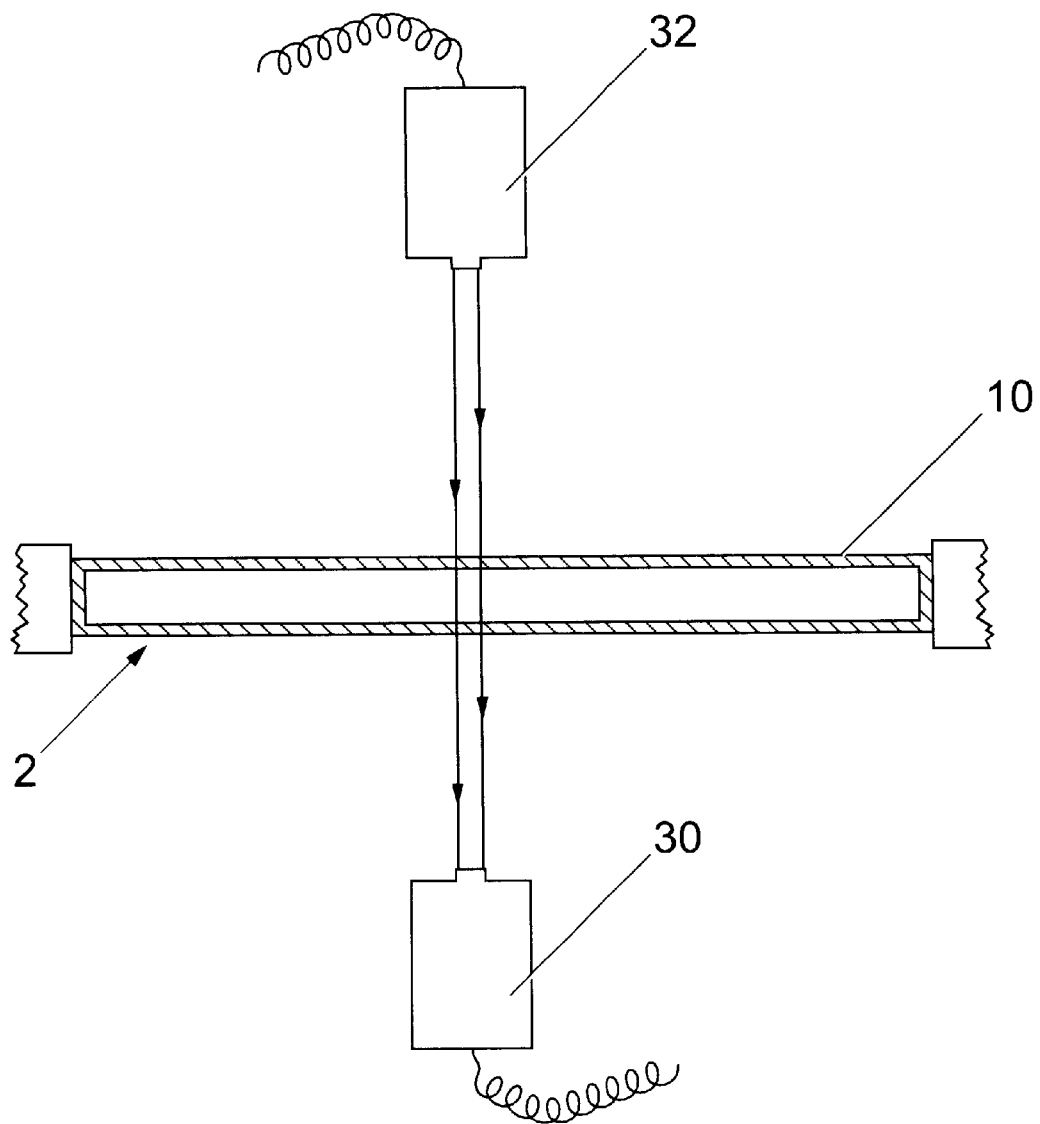
FIG. 1b is a schematic cross-sectional side view through a portion of the rotor of FIG. 1a with a microhaematocrit tube located in one of the slots.

FIG. 1b schematically illustrates a cross-section of a portion of rotor 4 and illustrates microhaematocrit tube 10 located within one slot 2. Also illustrated is a light source 30, which in the embodiment illustrated is an infra-red laser emitting light of wavelength 780 nm. Where permitted by the sample, the light source can pass through the microhaematocrit tube 10 and through slot 2 and be detected by the sensor 32.

Whilst four slots 2 are illustrated in FIG. 1b, the invention is not limited to this arrangement. For example, rotor heads having two, six or eight slots may be provided; the only requirement is for the centrifuge rotor to be balanced and for the analyser connected to the sensor 32 to be able to distinguish between each sample. That is, the interval between samples must be within the capability of both sensor 32 and the analyser (not shown).

In FIG. 1b the light source and detector 32 are shown located in a particular position having regard to the length of the microhaematocrit tube 10. The method of the present invention envisages that the light source 30 and the sensor 32 should be moveable along the radius of the rotor such that the full length of tube 10 may be scrutinised. Naturally, any movement of light source 30 and sensor 32 should be synchronised carefully.

EXAMPLE 1

An ESR test is to be carried out as a preliminary screening test on a sample of blood taken from a patient.

Blood drawn from the patient is added to a collection tube containing an appropriate anticoagulant. A sample of blood is then drawn by capillary action into a microhaematocrit tube (vol≦50 μl) so that the tube is approximately three-quarters filled with blood. Alternatively blood from a finger, thumb or ear lobe prick can be drawn into a microhaematocrit tube coated internally with an appropriate anticoagulant. This gives a significant advantage over existing methods for the following reasons:

a) The volume of blood required for the test is much smaller. (The microhaematocrit tube used is much smaller than the traditional Westergren or Wintrobe tube.)

b) It is possible to obtain a sufficiently large blood sample from a finger or ear lobe prick.

Figure 2A:
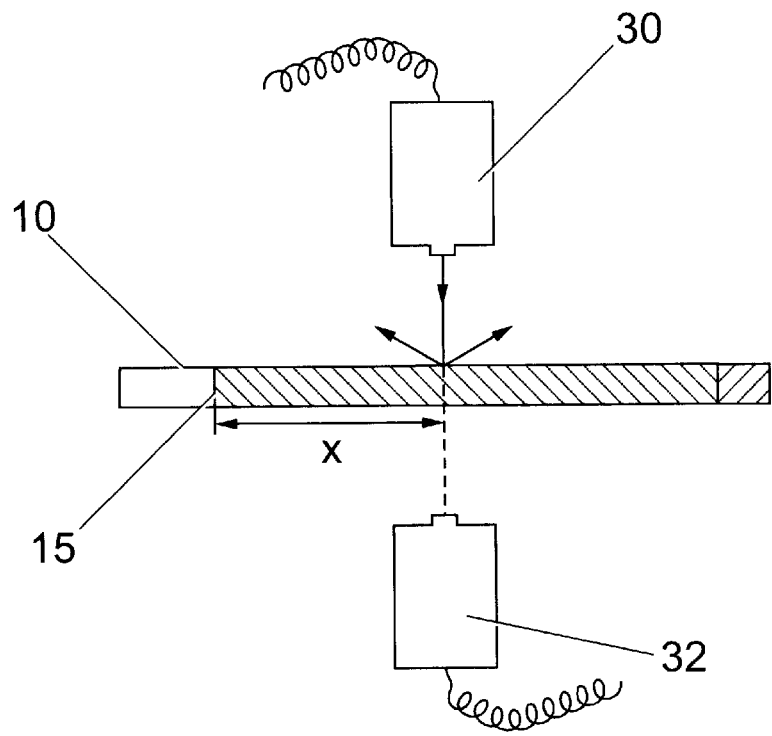
FIG. 2a is a microhaematocrit tube filled with whole blood prior to the commencement of centrifugation and showing the position of the optical source and sensor.

The microhaematocrit tube is sealed and loaded into a centrifugal device (autocentrifuge)—see FIG. 2a. A device such as the VS200 device described in WO-A-94/18557 may be used.

The autocentrifuge measures automatically the length of the column of blood in the microhaematocrit tube using an infra-red laser scanning arm which is positioned so that the laser beam passes through an appropriate portion of the microhaematocrit tube. As the centrifuge motor is started a timer is switched on. Whilst the sample is centrifuged, the laser beam will scan the sample once per revolution. Thus, for a microhaematocrit tube spinning at 600 rpm the laser beam will reach the sample 10 times every second. The automatic measurement occurs during the process of centrifugation.

In this example, the tube 10 may be spun for 2 minutes at a speed of 600 rpm. At the end of the centrifugation cycle, the infra-red scanner has determined the distance the cells have travelled along the haematocrit tube in the 2 minute centrifugation cycle.

Alternatively, referring to FIG. 2a, the optical source 30 and sensor 32 are positioned over the microhaematocrit tube 10 a pre-set distance X from the blood/air interface 15. In the device of WO-A-94/18557 distance X will be approximately 15 mm from the blood/air interface of a three-quarters filled tube. The centrifuge may include an automatic timer which records a time since commencement of centrifugation against each reading from the laser. Centrifugation continues until red blood cells begin to precipitate past the fixed position of the laser beam, at which point sensor 32 will begin to detect light passing through the sample.

Figure 2B:
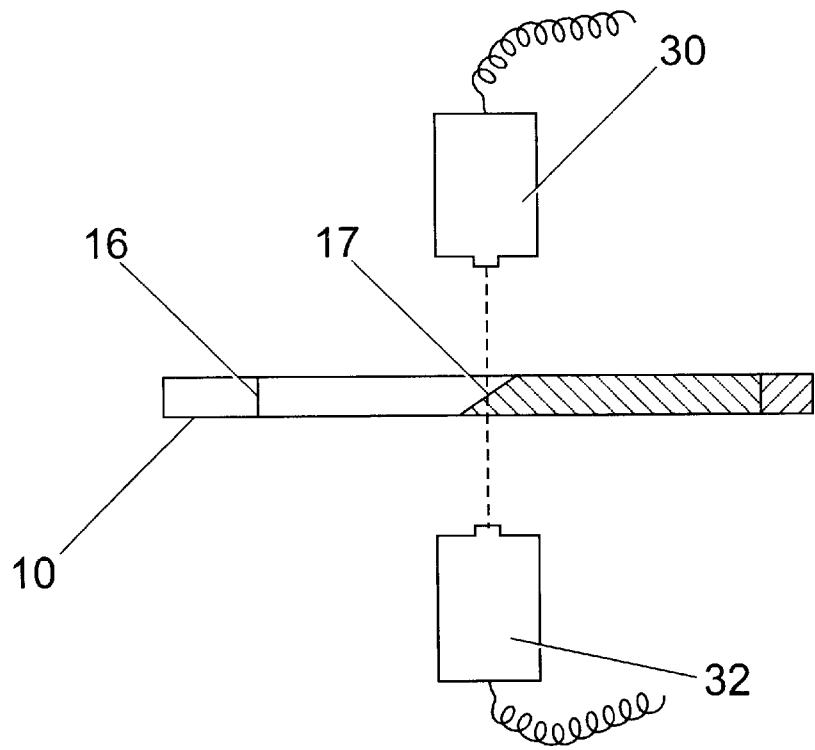
FIG. 2b is a microhaematocrit tube during ESR measurement and illustrating the development of an angled interface and the detection thereof.

As indicated in FIG. 2b, the plasma/red blood cell interface 17 is angled and the degree of this angle indicates the presence of immature red cells in the sample (reticulocytes) or other low density particles. Depending on their presence or absence the slope may be very shallow or almost vertical.

Diagnostic information on the composition of the blood may be obtained from the slope of the interface which can be identified clearly. In the method described thousands of readings are taken during the analysis. Thus depending on the conditions set (i.e. speed and diameter of rotor and length of blood column) the time taken for the blood to travel distance X and the slope of the interface provide good ESR data.

This information can be automatically correlated with the reading from the optical sensor 32.

The erythrocyte sedimentation rate (ESR) is then calculated automatically by the device and expressed in mm/minute or other suitable units.

The ESR may also provide information on the plasma viscosity which can yield further useful diagnostic data to the clinician.

Other tests may then be carried out on the blood sample, for example to determine the haemoglobin content and packed cell volume (PCV) ie the ratio of red cells to plasma. Advantageously, ESR determination is followed automatically by a PCV (packed cell volume) reading. To determine PCV of red blood cells, the post-ESR sample may be centrifuged at higher speeds (for example 10,500 rpm) to cause close packing of the red blood cells. The red blood cell/plasma interface can then be remeasured and the ESR adjusted to take account of an abnormality in the red blood cell concentration.

The ESR, as measured using the method of the invention, can be used as an indication of a variety of diseases or to monitor the progress of a particular disease in the patient.

EXAMPLE 2

Measurement of plasma fibrinogen uses the same apparatus (autocentrifuge) as used to test ESR and plasma viscosity in Example 1 above.

Figure 3A:
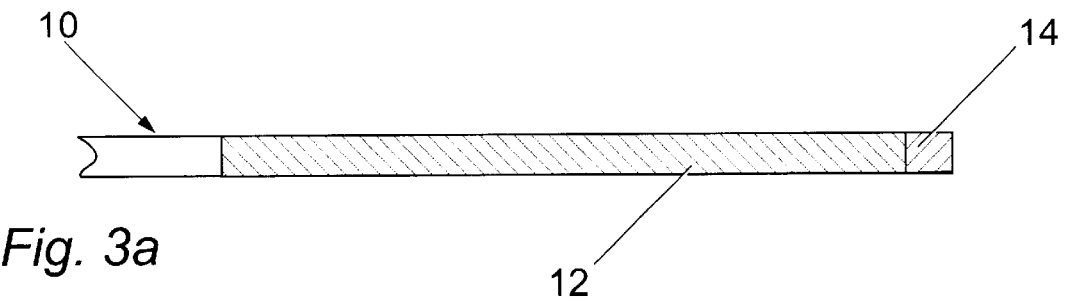
FIG. 3a is a microhaematocrit tube filled with blood for use in a method according to the invention for measuring plasma fibrinogen.

The measuring procedure is as follows: As illustrated in FIG. 3a, a microhaematocrit tube 10 is three-quarter filled with anticoagulated blood. The blood 12 in the tube 10 is uncentrifuged at this stage and a tube sealant 14 is provided at one end of the tube 10.

The tube 10 is placed in slot 2 of rotor 4 of the type shown in FIG. 1a located in the autocentrifuge (not shown).

The tube 10 is centrifuged at a speed of 10,500 rpm for 5 minutes.

Figure 3B:
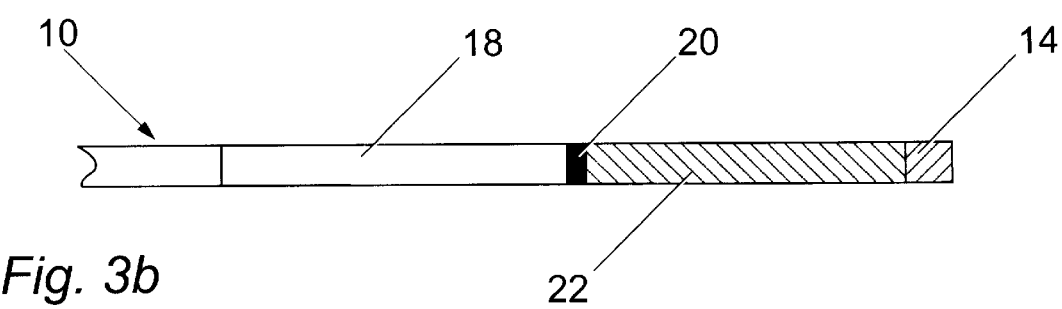
FIG. 3b is the tube of FIG. 3a after a first centrifugation of five minutes.

FIG. 3b shows the tube 10 after this first centrifugation stage.

From left to right in FIG. 3b, there is an air/plasma interface 16, followed by plasma 18 containing fibrinogen in solution, a buffy coat layer 20 (ie white blood cells and platelets) and packed red blood cells 22. The interface 16 in the centrifuged tube is scanned by the optical system of the autocentrifuge and identified.

Figure 3C:
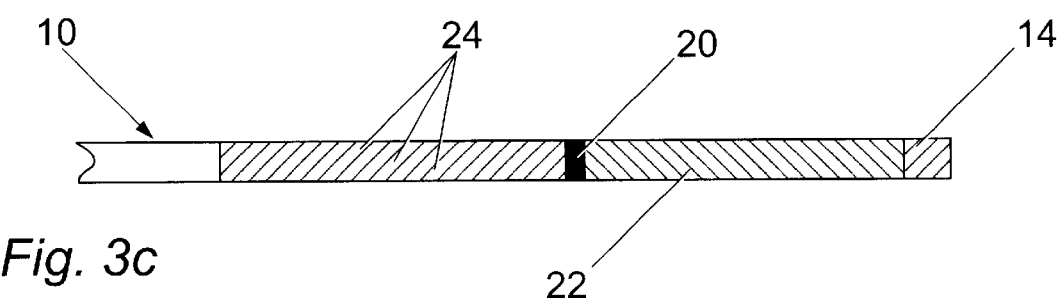
FIG. 3c is the tube of FIG. 3b after incubation at 56 to 58° C. for three minutes.

The tube 10 is removed from the autocentrifuge and incubated for 3 minutes at 56 to 58° C. which precipitates the fibrinogen from the plasma. The plasma 18 containing precipitated fibrinogen 24 can be seen in FIG. 3c.

The tube is replaced in the autocentrifuge and centrifuged again for 2 to 3 minutes at a speed of 10,500 rpm.

Alternatively, the incubation stage may occur automatically within the centrifuge. The tube is then scanned again by the optical sensor and the position of the interfaces measured again.

Figure 3D:
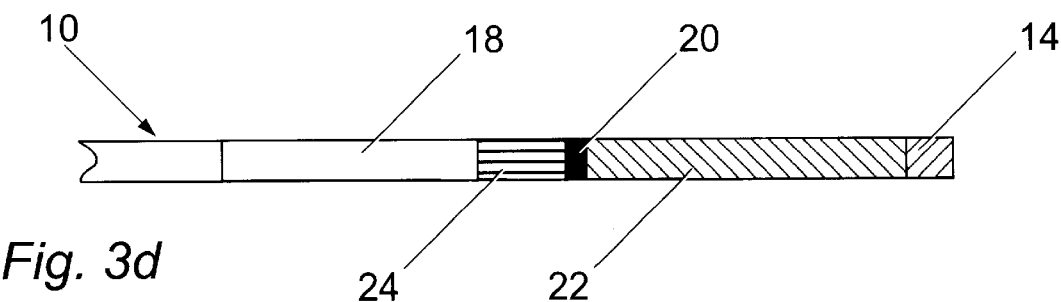
FIG. 3d is the tube of FIG. 3c after precipitation of fibrinogen following a second centrifugation of five minutes.

As can be seen in FIG. 3d, the fibrinogen 24 has precipitated onto the buffy coat layer 20 and has become packed. The analyzer automatically calculates the difference in buffy coat layer length in the tube and then calculates the fibrinogen concentration.

It is necessary to perform a total protein measurement on the sample to calculate the fibrinogen concentration.

The methods described have the advantage that the length of time to obtain the test results is significantly reduced as is the volume of blood required.

Modifications and improvements may be made to the foregoing without departing from the scope of the invention.

What is claimed is:

1. A method of measuring erythrocyte sedimentation rate, plasma viscosity or plasma fibrinogen of a blood sample wherein sedimentation of particles in the sample is accelerated by application of a centrifugal force to the sample, characterized in that said measurement is taken during centrifugation of the sample.

2. The method as claimed in claim 1, wherein said sample is monitored once per revolution.

3. The method as claimed in any one of claims 1 to 2 wherein said sample is in the form of a column and is centrifuged with the longitudinal axis of said column being maintained in the horizontal plane.

4. The method as claimed in claim 3 wherein the angle of the interface between the red blood cell phase and the plasma phase of the separating sample is measured.

5. The method as claimed in any one of claims 1 to 4 wherein said sample is monitored by measuring IR absorbance.

6. The method as claimed in claim 5 wherein the IR light source is an IR laser.

7. The method as claimed in any of claims 1 to 6 wherein the development of the interface between the red blood cell phase and the plasma phase and the movement of that interphase is monitored.

8. The method as claimed in any one of claims 1 to 7 wherein the sample is centrifuged at a speed of 500–4,000 rpm and the erythrocyte sedimentation rate is determined.

9. The method as claimed in claim 8 wherein the PCV of the sample is automatically determined and used to correct the ESR measurement.

10. The method as claimed in any one of claims 1 to 7 wherein the sample is centrifuged at a speed of 8,000 rpm or greater following precipitation of fibrinogen and the amount of plasma fibrinogen is determined.

* * * * *